(12) United States Patent
Schwartz et al.

(10) Patent No.: US 9,011,388 B2
(45) Date of Patent: Apr. 21, 2015

(54) PASSIVE SAFETY PORTAL DEVICE

(75) Inventors: Lori Schwartz, Lino Lakes, MN (US); Ronald G. Travis, Spring Lake Park, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 658 days.

(21) Appl. No.: 12/801,349

(22) Filed: Jun. 4, 2010

(65) Prior Publication Data
US 2011/0301542 A1 Dec. 8, 2011

(51) Int. Cl.
A61M 5/32 (2006.01)
A61M 5/162 (2006.01)
A61M 5/158 (2006.01)
A61M 25/06 (2006.01)

(52) U.S. Cl.
CPC ........... *A61M 5/1626* (2013.01); *A61M 5/3273* (2013.01); *A61M 2005/325* (2013.01); *A61M 5/158* (2013.01); *A61M 25/0618* (2013.01)

(58) Field of Classification Search
CPC . A61M 5/322; A61M 5/3234; A61M 5/0631; A61M 5/3273; A61M 5/3271; A61M 5/3243; A61M 5/3216
USPC .............................. 604/110, 164.08, 198, 263
See application file for complete search history.

(56) References Cited

U.S. PATENT DOCUMENTS

| | | | |
|---|---|---|---|
| 4,000,739 A * | 1/1977 | Stevens .......................... 604/537 |
| 4,929,241 A | 5/1990 | Kulli | |
| 4,944,725 A | 7/1990 | McDonald | |
| 4,964,854 A | 10/1990 | Luther | |
| 4,978,344 A | 12/1990 | Dombrowski et al. | |
| 5,300,045 A | 4/1994 | Plassche, Jr. | |
| 5,322,517 A | 6/1994 | Sircom et al. | |
| 6,537,259 B1 * | 3/2003 | Niermann ...................... 604/263 |
| 6,595,954 B1 | 7/2003 | Luther et al. | |
| 6,613,015 B2 | 9/2003 | Sandstrom et al. | |
| 6,719,721 B1 | 4/2004 | Okazaki et al. | |
| 7,438,703 B2 | 10/2008 | Barrus et al. | |
| 7,510,543 B2 | 3/2009 | Michels et al. | |
| 7,549,976 B2 | 6/2009 | Michels et al. | |
| 7,569,033 B2 | 8/2009 | Greene et al. | |
| 7,597,681 B2 | 10/2009 | Sutton et al. | |
| 7,632,243 B2 | 12/2009 | Bialecki et al. | |
| 7,988,664 B2 * | 8/2011 | Fiser et al. .................... 604/110 |

(Continued)

OTHER PUBLICATIONS

PCT International Search Report issued by the ISA/KR on Feb. 22, 2012.

(Continued)

*Primary Examiner* — Scott Medway
(74) *Attorney, Agent, or Firm* — Louis Woo (57) ABSTRACT

A portal access assembly includes an inserter that has a needle, a cap moveable along the length of the needle and an infuser having a cannula through which the needle extends. A safety mechanism inside the cap allows the needle to be moved relative to the cap so long as the shaft of the needle biases against an edge of one of the legs of the mechanism. After the cannula is properly positioned in the implanted port to establish a fluid path between the port and the infuser, the needle is removed by being pulled upwards until it no longer biases the one leg of the mechanism. At which time the safety mechanism fixedly captures the needle inside the cap to prevent the contaminated tip of the needle from being exposed to the environment. At the same time, the cap is detached from the infuser.

9 Claims, 5 Drawing Sheets

(56) References Cited

U.S. PATENT DOCUMENTS

| | | |
|---|---|---|
| 8,109,905 B2 * | 2/2012 | Saulenas et al. ............... 604/110 |
| 8,162,889 B2 * | 4/2012 | Swisher et al. ............... 604/162 |
| 2002/0099339 A1 * | 7/2002 | Niermann ..................... 604/263 |
| 2003/0040724 A1 * | 2/2003 | Lynn ............................ 604/256 |
| 2004/0133167 A1 | 7/2004 | Ferguson et al. |
| 2005/0004532 A1 * | 1/2005 | Woehr et al. .................. 604/263 |
| 2005/0075609 A1 | 4/2005 | Latona |
| 2005/0096592 A1 * | 5/2005 | Carlyon et al. ............... 604/110 |
| 2005/0182363 A1 * | 8/2005 | Kulli ............................. 604/110 |
| 2007/0149920 A1 | 6/2007 | Michels et al. |
| 2007/0191771 A1 | 8/2007 | Moyer |
| 2009/0163861 A1 * | 6/2009 | Carlyon ........................ 604/110 |

OTHER PUBLICATIONS

Supplementary European Search Report in related EP application No. 11790109.0, mailing date Dec. 4, 2013 from the European Patent Office.

* cited by examiner

PASSIVE SAFETY PORTAL DEVICE

FIELD OF THE INVENTION

The present invention relates to a device for accessing a portal reservoir, and particularly to a passive portal reservoir access safety needle device that automatically envelopes the contaminated tip of the needle of the device when the needle is removed from the portal reservoir.

BACKGROUND OF THE INVENTION

Long term intravenous therapy to a patient often requires that a portal reservoir (also may be referred to as port or portal) be implanted to the patient. The medicament stored in the port is fed slowly to an inside body area of the patient by way of a catheter tube connected to the port. To refill the port, conventionally a blunt cannula with a needle or trocar extending therethrough with the tip of the needle extending beyond the distal end of the blunt cannula is inserted through the skin of the patient into the port through its septum. The blunt cannula extends from the bottom surface of an infuser or infusion site that has a dome shaped housing having a septum top through which the needle extends into the blunt cannula. The domed housing has connected thereto a catheter tube, which in turn may be connected to the liquid medicament that is to be fed into the port. The top of the housing of the infuser is usually made from a resealable material such as rubber or silicone, so that when the needle is withdrawn from the blunt cannula and then the housing, the top of the infuser is resealed.

As with the use of any needle or sharps, there is always a chance that the user, or a bystander, may be accidentally pricked by the contaminated needle when it is removed from the patient, as the tip of the needle is contaminated with the fluid from the patient.

To prevent potential diseases and infections due to exposure to a contaminated needle, the prior art discloses a number of devices that prevent the tip of the needle from being exposed, after it is withdrawn from the blunt cannula. U.S. Pat. No. 6,613,015, assigned to the assignee of the instant application and the product covered thereby marketed under the trade name GRIPPER® PLUS, discloses the use of a right angle needle which, when withdrawn from the patient, has its tip secured to a well at the base of the inserter. Other patents by the assignee of the instant application include U.S. Pat. Nos. 7,510,543 and 7,549,976 which disclose a similar right angled needle that uses a portion of the base to prevent the contaminated tip of the needle from being exposed to the environment. For the '543 and '976 patents, the contaminated tip of the needle is maintained within the base of the inserter. The disclosure of the '015, '543 and '976 patents are incorporated by reference herein. The device sold under the aforenoted patents include the GRIPPER® MICRO, as well as the GRIPPER® PLUS. Another right angle needle that is entrapped as it pivots out of the blunt cannula is disclosed in U.S. Pat. No. 6,719,721. In all of the above-noted patents, insofar as the needle is a right angle needle, there requires a pivotal movement of an inserter arm.

The instant invention eliminates the need for a pivot arm and pivotal movement therefor, and at the same time allows for a passive and automatic capture of the contaminated tip, when the inserter is removed from the infuser.

SUMMARY OF THE PRESENT INVENTION

The port access assembly of the instant invention has an inserter that includes a handle and a needle or trocar that extends downwardly from the handle along a longitudinal axis. The needle is insertable into the infuser or infusion site so that it would go through the infuser and into the blunt cannula that extends from the bottom or bottom surface of the infuser. A cap is slidable along and relative to the needle, and is movable between a position adjacent to the handle to the distal portion of the needle. The cap has a top circumferential turret portion about which the lower portion of the handle may be form-fittingly mounted so that the inserter and the cap can be removably coupled, with the needle extending through an opening at the bottom of the cap. The exposed needle is inserted through the domed housing or base of the infuser, as the bottom of the cap rests on top of the infuser. The length of the needle is such that its distal tip extends beyond the distal end of the blunt cannula of the infuser. When thus assembled, the port access assembly is in a ready to use state whereby the combination of the inserter, cap and infuser are aligned along the longitudinal axis and may be placed vertically over the area of the patient that superposes over the implanted port, so that the needle and the blunt cannula fitted thereabout may be inserted into the patient to effect or establish a through passage to the implanted port.

The needle may be moved relative to the cap and the infuser without being completely removed from the infuser so that the needle may be retracted from the implanted port to allow blood or fluid return from the implanted port to the blunt cannula, thereby allowing a clinician to verify that a fluid path has been correctly established by the cannula between the infuser and the port. The needle can be removed completely from the infuser thereafter.

The cap has proximate to an opening at its bottom a first locking mechanism possibly in the form of fingers that engage to a second locking mechanism possibly in the form of an annular groove with an upper protrusion that circumscribes an opening at the top of the infuser. When the needle is inserted through the opening at the bottom of the cap, the fingers are biased by the outer circumferential surface of the shaft of the needle, so that the cap and the infuser are fixedly or non-detachably engaged to each other. The inserter assembly and the infuser can thus be shipped as a single unit, with the inserter, cap and the infuser being coupled to each other.

After a fluid passage has been properly established between the infuser and the implanted port, an upwards movement of the handle relative to the infuser would retract the needle from the blunt cannula and then the infuser. The cap may then be separated from the infuser as the fingers at the bottom opening of the cap are no longer biased into the groove at the opening at the top of the infuser by the shaft of the needle. In practice, when the inserter handle is pulled upwards away from the infuser, after the needle passes the opening at the base of the cap, as the inserter handle is continuously pulled upwards, the fingers at the bottom opening of the cap would flex inwards toward the center of the opening due to their interaction with the circumferential protrusion at the top opening of the infuser, until the fingers are pulled past the protrusion to thereby separate the cap from the infuser.

There is a safety or shield mechanism inside the cap that guides the needle to slidably move relative to the cap when the cap is coupled or engaged to the infuser, and to prevent further movement of the needle, once the needle is withdrawn completely out of the infuser into the interior cavity of the cap, so that the contaminated tip of the needle could no longer be re-exposed to the environment. To achieve this end, the safety mechanism in the cap of the inserter assembly of the instant invention may be in the form of a clip that has two legs connected by a center bridge section substantially orthogonal to the legs, with an upper or a first one of the legs having an aperture through which the needle passes while the lower or second of the legs has an edge biased by the shaft of the needle when the needle is slidably movable relative to the cap. When the inserter handle is moved vertically upwards to remove the needle from the blunt cannula and then the infuser, the needle is moved upwardly with the movement of the handle.

When, due to the upwards movement of the needle, the edge of the second leg of the clip inside the cap is no longer biased by the shaft of the needle, the clip, which is being biased by the needle shaft in a given direction inside the cap, is moved into a canted position so that the second leg intercepts the longitudinal axis along the path of the needle and the surface of the second leg facing the first leg is moved into a position to block any downwards movement of the needle. At the same time, due to the canted positioning of the clip, the plane of the aperture is aligned in an offset manner relative to the longitudinal axis of the needle such that the internal circumferential edge of the aperture at the first leg forcibly abuts the shaft of the needle to thereby prevent further upwards movement of the needle. Thus, the distal portion of the needle is fixedly captured by the two legs of the clip inside the cap. The distal portion of the needle, in particular the contaminated tip of the needle, is thereby prevented from being exposed to the environment.

The present invention is therefore directed to an apparatus for establishing a fluid path to an implanted port. The apparatus has an infuser including a base having a plane and a cannula having a distal end extending from the base. The infuser is adapted to be placed onto a patient with the cannula inserted into the patient to be in communication with the port. The apparatus also has an inserter including a needle having a tip at its distal end, the inserter positionable over and orthogonal to the plane of the base of the infuser with the needle extending through the cannula and the needle tip extending beyond the distal end of the cannula. The apparatus further includes a cap removably attached to the infuser that is slidable along and movable relative to the needle to a position that covers the distal tip of the needle. A safety mechanism is provided in the cap to guide the needle to slidably move relative to the cap, the mechanism being biased by the needle. The apparatus is in a ready to use state when the needle extends through the cannula with the cap removably attached to the infuser. When the needle is removed from the cannula in a used position, no longer biased by the needle, the safety mechanism in the cap prevents the tip of the needle from re-emerging from the cap and prevents further movement of the cap relative to the needle. At the same time, the cap can be separated from the infuser.

The present invention is also directed to a medical device that includes an infuser having a base and a cannula extending from the base; an inserter having a handle with a needle attached thereto, the inserter positionable over the infuser with the needle movably extending through the base into the cannula of the infuser; a cap having a top and a bottom, respective top and bottom openings at the top and bottom of the cap in alignment along the vertical axis, the cap slidably movable relative to the shaft of the needle, the bottom of the cap positionable onto the top of the infuser; a shield means in the cap operable between a first position and a second position in response to whether an edge of the shield means is biased by the needle, wherein the shield means is in the first position when at least a portion of the needle is extended beyond the edge of the shield means, and wherein the shield means is in the second position when the edge of the shield means is not biased by the needle as the needle is removed from the infuser; the shield means having a stop that prevents the tip of the needle from re-emerging from the cap when the shield means is in its second position.

The invention is moreover directed to a combination having an inserter having a vertically downwards extending needle; a cap slidably mounted about the shaft of the needle, the cap having a cavity; a clip in the cavity of the cap having two legs, a first leg having an aperture through which the needle passes when the clip is in a first position, a second leg having an edge biased by the shaft of the needle when the clip is in the first position; biased means in the cap to exert a biasing force against the clip so that when the edge of the second leg is not biased by the shaft of the needle the clip is moved to a second position in the cavity of the cap; an infuser having a top onto where the cap rests and a base wherefrom a cannula extends; the needle having a tip extending beyond the plane of the second leg when the needle extends through the cannula and the cap rests on the top of the infuser; wherein when the needle is pulled upwardly out of the infuser and no longer biases the edge of the second leg, the needle is prevented from further upwards and downwards movements by the first and second legs, respectively.

The present invention port access assembly is therefore a passive safety device that automatically captures the contaminated tip of a needle when the needle is withdrawn from an implanted port after a fluid path has been established between an infuser and the implanted port.

BRIEF DESCRIPTION OF THE FIGURES

The present invention will become apparent and the invention itself will be best understood by reference to the following description taken in conjunction with the accompanying drawings wherein.

DETAILED DESCRIPTION OF THE INVENTION

Figure 1:
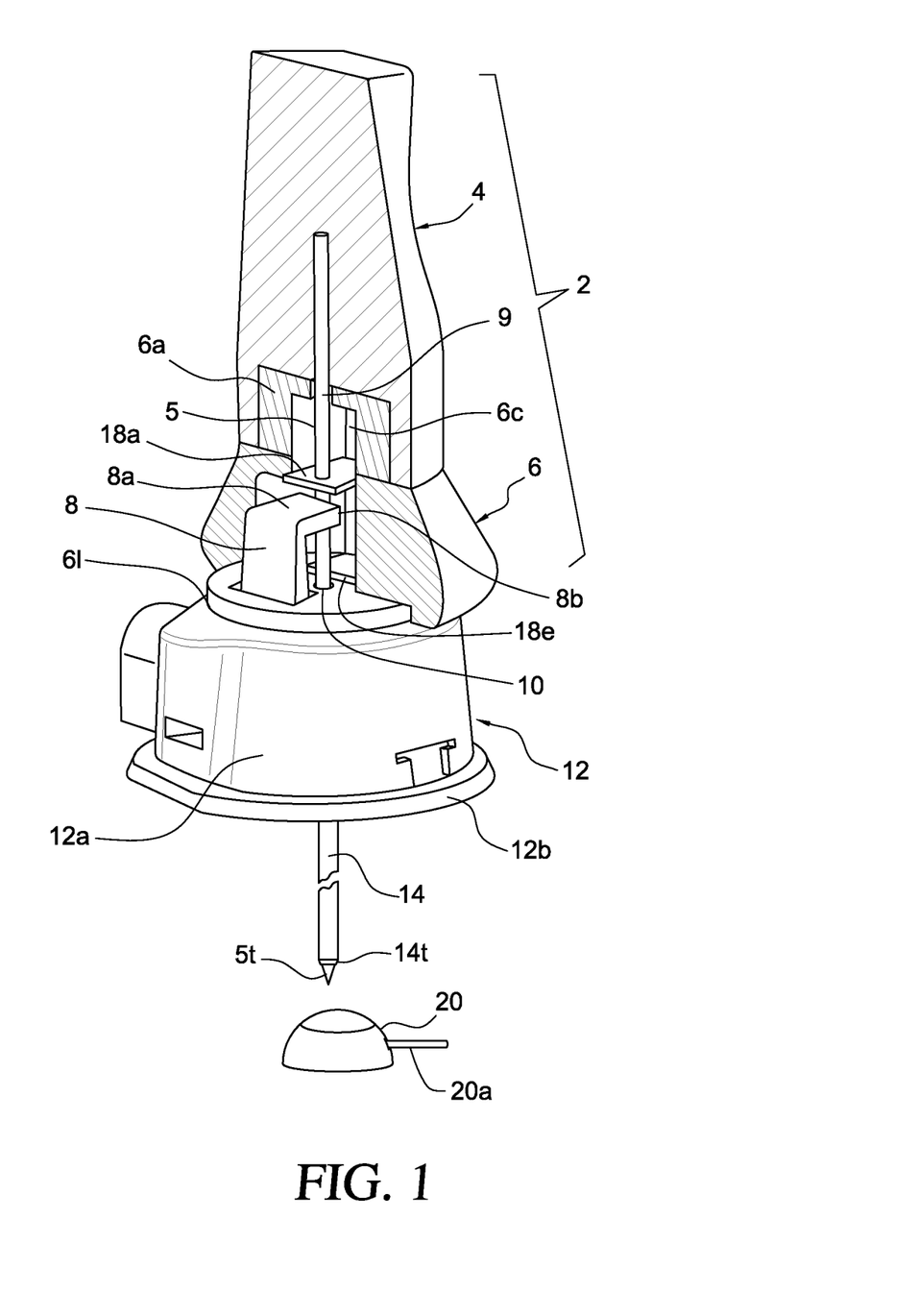
FIG. 1 is a partial cross-sectional view of the port access assembly of the instant invention.
Figure 2:
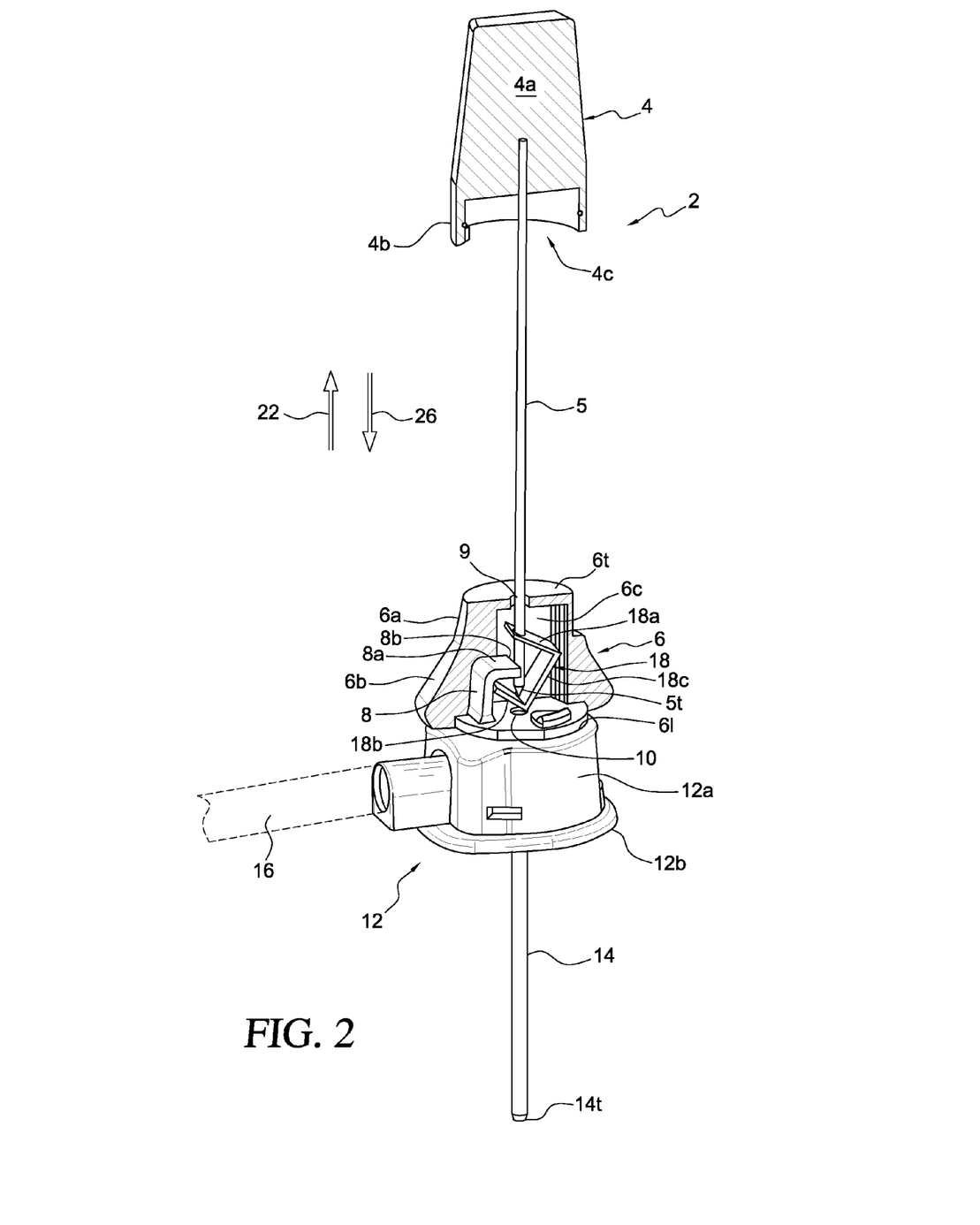
FIG. 2 is a partial cross-sectional view of the port access assembly of the instant invention with the needle shown having been withdrawn into the cap of the port access assembly.
Figure 3:
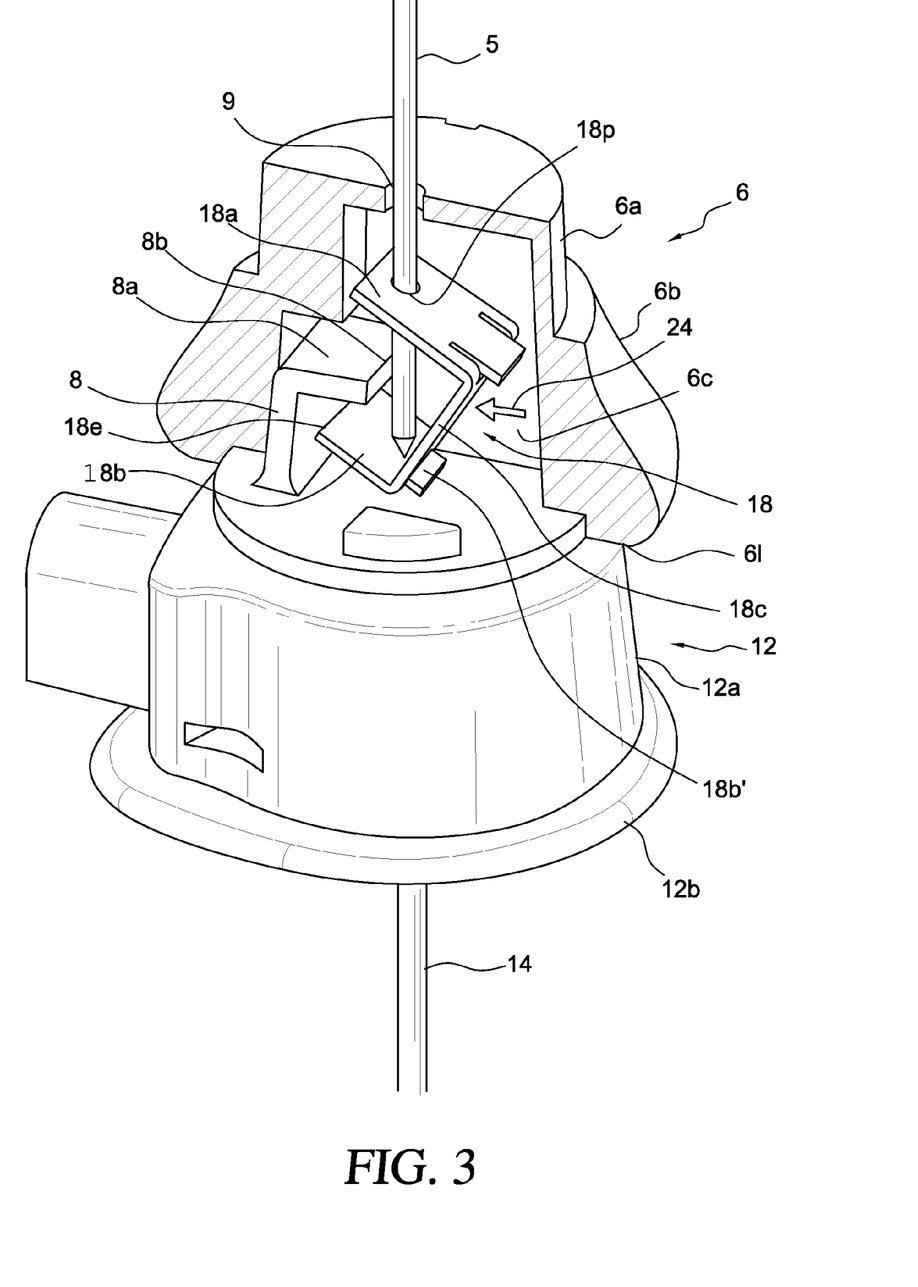
FIG. 3 is another cross-sectional view of the interior cavity of the protective cap of the port access assembly of the instant invention showing the safety clip in a canted position.

With reference to FIGS. 1-3, the portal or port access assembly of the instant invention is shown to include an inserter 2 having a handle 4 and a needle or trocar 5 extending downwardly in a vertical direction from handle 4 along the longitudinal axis of the needle. Handle 4 has a main portion 4a and a lower portion 4b that defines a bore 4c.

Mounted about needle 5 and slidable relative to and movable along the length of needle 5 is a cap or housing 6 that has an upper circumferential turret portion 6a and a semi-cone shaped lower portion 6b. Cap 6 has a top portion or top 6t, and a bottom portion or bottom 6l that is joined to or is integral with the distal bottom of lower portion 6b. There is extending upwardly from bottom 6l a reverse L-shaped extension 8 that has a finger portion 8a having an edge 8b that makes contact with, or biases, the shaft of needle 5. Tip 5t of needle 5 is shown to extend through an opening 10 at bottom 6l and from there through infuser or infusion site 12 and the blunt cannula 14 that extends from the bottom or base 12b of infuser 12. As shown in FIG. 1, handle 4 is fittingly coupled to cap 6 as bore 4c of lower portion 4b of handle 4 removably mates to the upper turret portion 6a of cap 6.

Infuser 12 has a dome shaped housing 12a that is in fluid communication with blunt cannula 14. Fluid or medication may be conveyed into housing 12a by a catheter tubing 16, shown in dotted line in FIG. 2, connected to infuser 12. Infuser 12 has a top or top portion 12t and a bottom or base portion 12b. A resealable septum 12d (FIG. 4) that is pierceable by needle 5 may be fixed to the lower surface of top 12a for example by gluing or bonding, so that as shown in FIG. 1, needle 5 extends through cap 6 and pierces through septum 12d into infuser 12, and from there extends through blunt cannula 14, its distal sharp tip 5t extending beyond the distal end of cannula 14.

A cavity 6c is formed in the interior of cap 6. Inside cavity 6c there is a safety mechanism in the form of a clip 18 that has a first or upper leg 18a and a second or lower leg 18b that are joined by a bridge section 18c that is substantially orthogonal to the two legs. As shown in FIG. 2, section 18c may comprise two spaced in parallel members each connecting the two legs. Leg 18b has an edge 18e, which is shown in FIG. 1 to be biased by the shaft of needle, as needle 5 extends from the upper opening 9 at the top of cap 6 through cavity 6c to the lower opening 10 at the bottom of cap 6.

As shown in FIG. 1, the bridge section 18c of clip 18 lies substantially in parallel to the longitudinal axis along which needle 5 vertically extends. The position of the port access assembly as shown in FIG. 1 may be referred to as the ready to use state or position. In this state, needle 5 may be moved vertically relative to cap 6 and infuser 12, so long as edge 18e of lower leg 18b of clip 18 is being biased by the shaft of needle 5. Thus, in the ready to use state, the shaft of needle 5 is biased by finger 8b of upright 8 integral to cap 6 while the shaft in turn biases against edge 18e of the lower leg 18b of clip 18. As a practical matter, by being able to upwardly move needle 5 relative to infuser 12 by pulling on handle 4, a clinician can determine whether or not blunt cannula 14 has been successfully positioned into the implant port 20, per shown in FIG. 1, by looking at the fluid or blood flash from the port.

The port access assembly of the instant invention may be placed by the clinician onto the area of the patient superposed over the port 20 that has been implanted into the patient so that the distal portion of cannula 14 including its distal end 14t, with needle tip 5t extending therefrom, may be inserted into port 20. Once the distal portion of cannula 14 is deemed to be properly positioned within port 20, needle 5 may be removed from cannula 14. A resulting fluid path is thus established between catheter tubing 16, infuser 12, cannula 14 and implanted port 20, with the medication supplied into port 20 output to the patient by means of port tubing 20a.

With reference to FIGS. 2 and 3, needle 5 is shown to have been removed from infuser 12. As shown, the distal tip 5t of needle 5 has been moved vertically upwards in the direction indicated by directional arrow 22 so that edge 18e of the lower leg 18b no longer is biased by the shaft of needle 5. A bias means such as a spring or an elastic flexible member provided in cavity 6c, identified by the bold arrow 24 in FIG. 3 for illustration purpose, applies a biasing force against bridge section 18c of clip 18, so that when edge 18e of leg 18b is no longer biased by the shaft of needle 5, per shown in FIG. 1, the force 24 against clip 18 would move clip 18 into the canted position as shown in FIGS. 2 and 3. As a result, leg 18b is positioned in the angled orientation as shown in FIGS. 2 and 3, thereby acting as a stop to entrap tip 5t of needle 5 and to prevent needle 5 from moving downwards, per indicated by directional arrow 26, once the needle tip 5t is trapped by leg 18b.

At the same time, as upper leg 18a is also oriented in a canted position, the internal circumferential edge of aperture 18p through which needle 5 passes is positioned at an angle offset to the longitudinal axis of needle 5, so that the edge of aperture 18b would forcibly abut the shaft of needle 5 and act to grasp or fixedly retain needle 5 to leg 18a. Simply put, the distal portion of needle 5 is held fixedly to and captured by clip 18 within cap 6.

Lower leg 18b has an extension 18b' that, once leg 18 is moved to its canted position, would coact against the top surface of bottom 6l of cap 6, so that the lower leg 18b is prevented from returning to its ready to use position as shown in FIG. 1. Accordingly, with clip 18 in the canted position as shown in FIGS. 2 and 3, needle 5 is prevented from moving upwardly per directional arrow 22 and downwardly per directional arrow 26, with tip 5t being trapped by leg 18b and its extension 18b'. Also, edge 18e of leg 18b comes into abutting contact with the underside of finger 8a of upright 8. Thus, as needle 5 is pulled upwardly per directional arrow 22 so that it no longer biases edge 18e of leg 18b of clip 18, the movement of needle 5 relative to cap 6 is stopped. And since clip 18 is now fixedly positioned in cavity 6s and leg 18b is in abutting relationship with upright 8, a further continuous upwards movement of handle 4 would separate cap 6, along with needle 5, from infuser 12, as clip 18 would act as a lift to move cap 6 in concert with the movement of needle 5 to separate cap 6 from infuser 12, so long as infuser 12 and cap 6 are not non-detachably coupled as will be explained below.

For the port access assembly of the instant invention, when the assembly is in the ready to use state as shown in FIG. 1, so that cap 6 and infuser 12 could be moved as a single unit, there are provided respective lock mechanisms at the interface between cap 6 and infuser 12. These respective lock mechanisms are further discussed hereinbelow.

Figure 4:
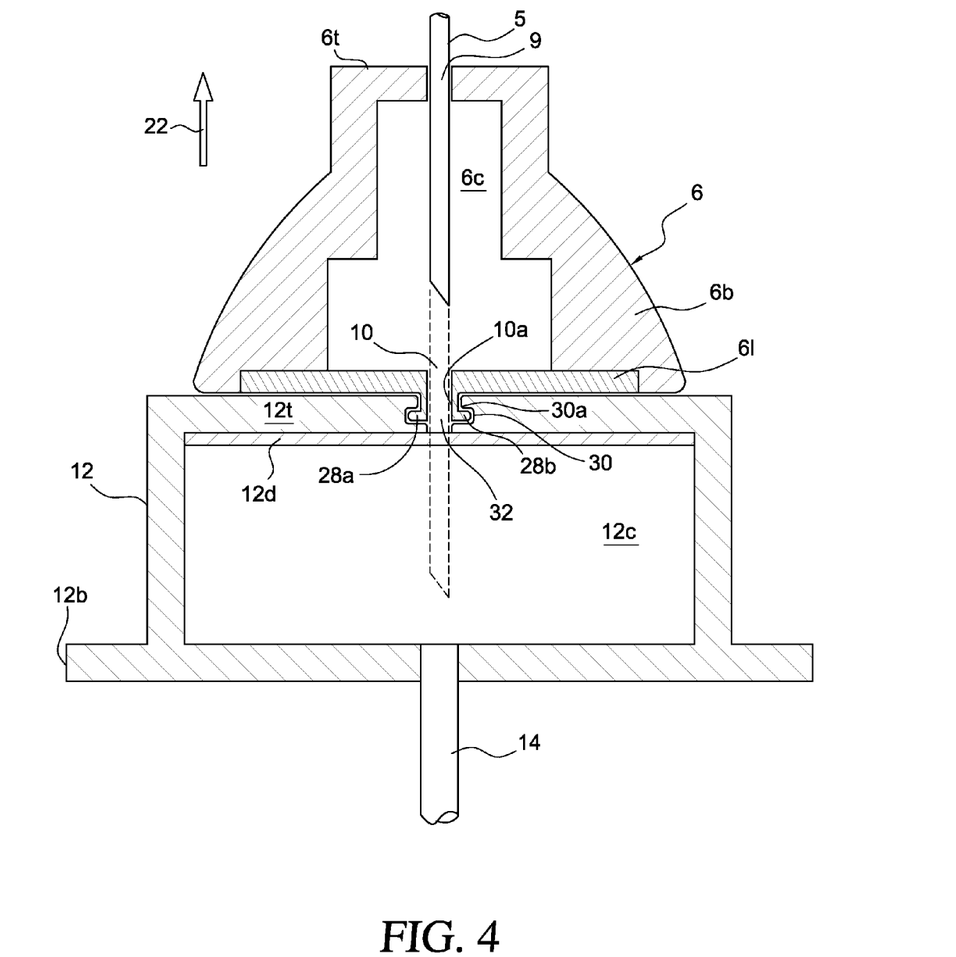
FIG. 4 is a cross-sectional view of the port access assembly of the instant invention showing the cap coupled to the infuser.

With reference to FIG. 4, there is shown at the bottom 6l of cap 6 two fingers 28a and 28b extending downwardly adjacent to lower opening 10 of cap 6. Fingers 28a and 28b engage with a circumferential groove 30 provided at the counterpart opening 32 at the top 12t of infuser 12. Fingers 28a and 28b may be considered as one lock mechanism and groove 30 and its upper protrusion 30a may be considered as another lock mechanism. As openings 10 and 32 are in alignment, a through path extends from cavity 6c of cap 6 to cavity 12c of infuser 12, ignoring for the moment the presence of resealable septum 12d bondedly affixed to the underside of top 12t of infuser 12. A through passage extends from cavity 12c to cannula 14, as is conventional for infusers.

Needle 5, in dotted line, is shown to extend from upper opening 9 at top 6t of cap 6 to lower opening 10 at bottom 6l of cap 6, and extends into cavity 12c of infuser 12. When thus positioned, the outer circumferential surface of needle 5 biases against the interior wall 10a of opening 10, so that fingers 28a and 28b are held in place in groove 30, resulting in cap 6 and infuser 12 being non-detachably coupled to each other.

When needle 5 is pulled into cavity 6c, per shown by the solid line, as the interior surface of opening 10, and particularly the extensions that connect fingers 28a and 28b to bottom 6l of cap 6 are no longer biased toward groove 30, with further upwards movement of needle 5, per designated by directional arrow 22 as described above, fingers 28a and 28b, due to the inherent elasticity of the medical plastics from which cap 6 and fingers 28a and 28b are made, would slightly bend inwardly to converge toward the center of opening 10, so as to disengage from groove 30 by being pulled past protrusion 30a. Consequently, cap 6 is disengaged or uncoupled from infuser 12. The elastomeric septum 12d then reseals cavity 12c of infuser 12 from the environment.

As described above, with the tip 5t of needle 5 being captured and fixedly housed in cavity 6c of cap 6, the removal of needle 5 by the pulling of handle 4 in the upwards direction relative to infuser 12 also results the removal of cap 6 from infuser 12, which is left on the patient, in one continuous vertical motion by the clinician. Medication may then be conveyed from infuser 12 to the implanted port 20 via cannula 14.

FIGS. 5a-5d illustrate the different stages of the movement of the inserter relative to the infuser of the instant invention port access assembly.

Figure 5A:
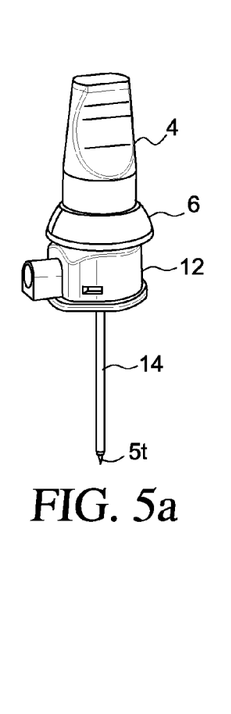
FIGS. 5a-5d are respective views of the port access assembly of the instant invention shown in the various stages where the inserter is being withdrawn relative to the infuser.

FIG. 5a is similar to FIG. 1 in that the handle 4 of inserter 2 is shown to be coupled to cap 6, which in turn rests on the top of infuser 12, with needle 5 extending though cap 6, infuser 12 and cannula 14 so that tip 5t of needle 5 extends beyond the distal end of cannula 14. In this ready to use state, as described above, cap 6 is fixedly coupled to infuser 12 so that the port access assembly is in one piece. The one piece assembly could then be readily positioned onto the area of the patient over the implanted port, so that only a simple vertical movement by the clinician is needed to insert the needle and cannula into the patient and position the cannula into the implanted port. Also, the one piece port access assembly allows the assembly to be shipped in the ready to use state.

Figure 5B:
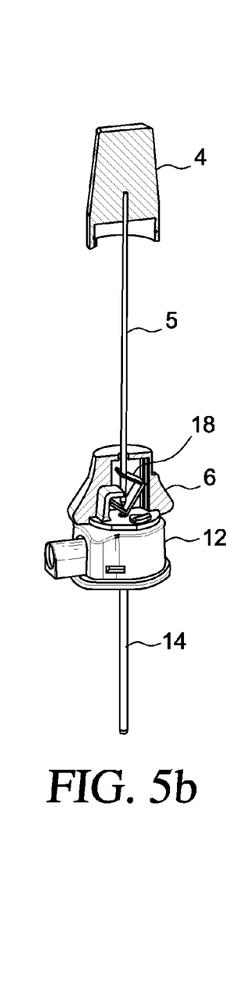
Figure 5C:
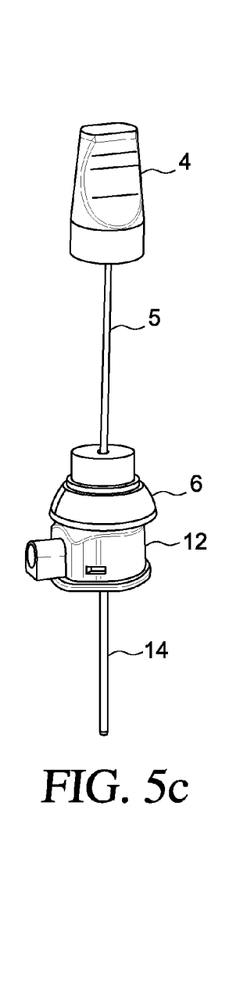
Figure 5D:
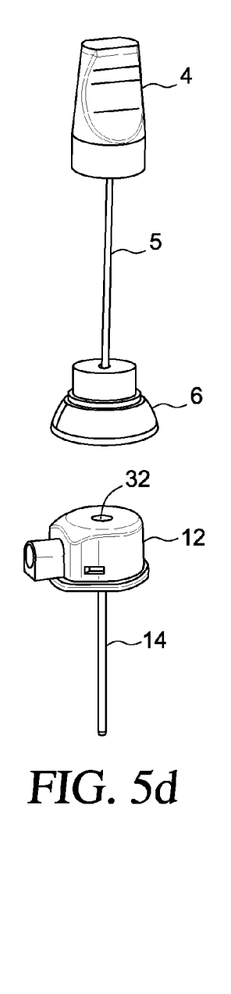

FIG. 5b is similar to FIGS. 2 and 3 in that it shows that needle 5 has been removed from infuser 12 and that the tip of the needle is captured in place in cap 6, by means of clip 18, as shown per the cross-sectional view of cap 6. FIG. 5c is the same as FIG. 5b except that it is in perspective view. FIG. 5d shows the complete disengagement or removal of cap 6 from infuser 12, with the tip of needle 5 being housed in cap 6.

It should be appreciated that the present invention is subject to many variations, modifications and changes in detail. Accordingly, the matter described throughout this specification and shown in the accompanying drawings should be interpreted as illustrative only and not in a limiting sense.

The invention claimed is:

1. Medical device to establish a fluid path to a port implanted in a patient, comprising:
    an infuser having a housing that forms a cavity with a top having a top surface and a lower surface, the top including an opening having a resealable septum fixed to the lower surface, a base having a cannula extending downwardly therefrom and a tubing connected to the housing to convey a medicament into the cavity, the base of the infuser is adapted to be placed onto an area of the patient superposed over the port so that the medicament in the cavity of the housing may be fed to the port;
    an inserter having a handle with a needle attached thereto, the inserter positionable relative to the infuser with the needle movably extending into the cavity of the housing and through the base into the cannula of the infuser;
    a cap having a top and a bottom having a bottom surface, respective top and bottom openings at the top and bottom of the cap in alignment along the vertical axis to enable only the needle to pass through, the cap slidably movable relative to the shaft of the needle, the bottom of the cap positionable onto the top surface of the infuser;
    a shield means in the cap operable between a first position and a second position in response to whether an edge of the shield means is biased by the needle, wherein the shield means is in the first position when at least a portion of the needle is extended beyond the edge to bias against the edge and maintain the shield means in the first position, and wherein the shield means is in the second position when the edge of the shield means is not biased by the shaft of the needle as the needle is removed from the infuser, the shield means having a stop that prevents the tip of the needle from emerging from the bottom of the cap when the shield means is in its second position;
    wherein the cap has at least one finger adjacent to its bottom opening that engages a groove formed at the inner circumferential surface of the opening at the top of the infuser, the finger being biased by the shaft of the needle when the needle is extended into the infuser and disengageable from the groove when the needle is removed from the infuser.

2. Medical device of claim 1, wherein the finger is a first lock mechanism adjacent to the bottom opening of the cap lockingly coupled with a second lock mechanism at the top of the infuser when the needle extends through the bottom opening of the cap into the infuser.

3. Medical device of claim 2, wherein the cap is separable from the infuser, the first lock mechanism at the bottom of the cap disengageable from the second lock mechanism at the top of the infuser when the needle is retracted upwards out of the bottom opening of the cap into the cap.

4. Medical device of claim 1, wherein the shield means comprises a clip having at least two legs, a first leg having an aperture through which the needle passes, a second leg of the clip having the edge against which the shaft of the needle biases when the clip is in the first position, the second leg acting to prevent the tip of the needle moving downwards from the cap when the clip is moved to its second position.

5. Medical device of claim 4, wherein the clip is moved to a canted position so that the one leg is at an angle relative to the needle to fixedly grasp the needle, the clip being fixed to the cap so that the removal of the needle from the infuser also removes the cap from the infuser.

6. Medical device of claim 4, further comprising bias means in the cap for forcing the second leg to move into the second position to prevent the tip of the needle from emerging out of the cap when the shaft of the needle is not in contact with the edge of the second leg.

7. Medical device of claim 1, wherein the inserter handle is vertically positioned relative to the infuser for inserting into the implanted port, and wherein with the infuser positioned on the patient and over the implanted port, a downward movement of the inserter would insert the needle and the cannula into the port to effect the fluid path between the infuser and the port.

8. Medical device of claim 4, wherein the finger of the cap biases the needle in an opposing direction as the edge of the other leg of the clip so long as the tip of the needle has not moved upwardly beyond the edge of the other leg of the clip.

9. Medical device of claim 2, wherein the finger extends downwardly adjacent to its bottom opening and wherein the second lock mechanism comprises a groove formed at the inner circumferential surface of the opening at the infuser.

* * * * *